United States Patent
Shakespeare et al.

(10) Patent No.: US 7,688,447 B2
(45) Date of Patent: Mar. 30, 2010

(54) COLOR SENSOR

(75) Inventors: Tarja T. Shakespeare, Kuopio (FI); John F. Shakespeare, Kuopio (FI)

(73) Assignee: Honeywell International Inc., Morristown, NJ (US)

( * ) Notice: Subject to any disclaimer, the term of this patent is extended or adjusted under 35 U.S.C. 154(b) by 794 days.

(21) Appl. No.: 11/362,582

(22) Filed: Feb. 24, 2006

(65) Prior Publication Data

US 2007/0153277 A1    Jul. 5, 2007

Related U.S. Application Data

(60) Provisional application No. 60/754,694, filed on Dec. 29, 2005.

(51) Int. Cl.
*G01J 3/46* (2006.01)
*G01N 21/25* (2006.01)

(52) U.S. Cl. ...................... 356/402; 356/417

(58) Field of Classification Search ............. 356/402, 356/417
See application file for complete search history.

(56) References Cited

U.S. PATENT DOCUMENTS

| | | | |
|---|---|---|---|
| 3,536,405 A | 10/1970 | Flower | |
| 3,802,774 A | 4/1974 | Eschler et al. | |
| 4,006,358 A | 2/1977 | Howarth | |
| 4,068,955 A | 1/1978 | Bodlaj | |
| 4,160,204 A | 7/1979 | Holmgren et al. | |
| 4,276,480 A | 6/1981 | Watson | |
| 4,288,691 A | 9/1981 | Horton | |
| 4,311,658 A | 1/1982 | Nicoll | |
| 4,376,946 A | 3/1983 | Kaminow et al. | |
| 4,439,038 A | 3/1984 | Mactaggart | |
| 4,490,845 A | 12/1984 | Steinbruegge et al. | |

(Continued)

FOREIGN PATENT DOCUMENTS

DE    3148076 A1    6/1983

(Continued)

OTHER PUBLICATIONS

Tarja Shakespeare and John Shakespeare, "Problems in colour measurement of fluorescent paper grades", Analytica Chimica Acta, 1999, pp. 227-242, vol. 380 issue 2-3, Elsevier Science B.V., Finland.

(Continued)

*Primary Examiner*—Roy Punnoose
(74) *Attorney, Agent, or Firm*—Munck Carter, LLP

(57) ABSTRACT

Devices, systems, and methods for measuring the color of a sample are disclosed. The exemplary device may have one or more light emitting diodes for directing a beam of ultraviolet light onto the sample and may also have one or more light emitting diodes for directing a beam of visible light onto the sample. The exemplary device may have a component for controlling the timing and power of operation of each light emitting diode. The exemplary device may also have at least one light detector for receiving the beam of light reflected from or transmitted through the sample and measuring at least one wavelength band of the received light. The exemplary device may further have a measurement analyzer for determining the color of the sample based on the measured light. The color may be determined for a specified illuminator incorporating effects of fluorescence.

23 Claims, 6 Drawing Sheets

U.S. PATENT DOCUMENTS

| | | | |
|---|---|---|---|
| 4,505,550 A | 3/1985 | Steinbruegge | |
| 4,565,444 A | 1/1986 | Mactaggart | |
| 4,592,043 A | 5/1986 | Williams | |
| 4,634,928 A | 1/1987 | Figueroa et al. | |
| 4,653,925 A * | 3/1987 | Thornton, Jr. | 356/419 |
| 4,699,510 A | 10/1987 | Alguard | |
| 4,708,483 A | 11/1987 | Lorenz | |
| 4,773,760 A | 9/1988 | Makkonen | |
| 4,786,817 A | 11/1988 | Boissevain et al. | |
| 4,797,246 A | 1/1989 | Reinke et al. | |
| 4,807,630 A | 2/1989 | Malinouskas | |
| 4,843,481 A | 6/1989 | Plummer | |
| 4,856,014 A | 8/1989 | Figueroa et al. | |
| 4,879,471 A | 11/1989 | Dahlquist | |
| 4,883,963 A | 11/1989 | Kemeny et al. | |
| 4,885,709 A | 12/1989 | Edgar et al. | |
| 4,928,013 A | 5/1990 | Howarth et al. | |
| 5,013,403 A | 5/1991 | Chase | |
| 5,015,099 A | 5/1991 | Nagai et al. | |
| 5,039,855 A | 8/1991 | Kemeny et al. | |
| 5,047,652 A | 9/1991 | Lisnyansky et al. | |
| 5,094,535 A | 3/1992 | Dahlquist et al. | |
| 5,122,974 A | 6/1992 | Chance | |
| 5,137,364 A | 8/1992 | McCarthy | |
| 5,166,748 A | 11/1992 | Dahlquist | |
| 5,172,005 A | 12/1992 | Cochran et al. | |
| 5,210,593 A | 5/1993 | Kramer | |
| 5,230,923 A | 7/1993 | Hirokawa et al. | |
| 5,235,192 A | 8/1993 | Chase et al. | |
| 5,276,327 A | 1/1994 | Bossen et al. | |
| 5,313,187 A | 5/1994 | Choi et al. | |
| 5,338,361 A | 8/1994 | Anderson et al. | |
| 5,365,084 A | 11/1994 | Cochran et al. | |
| 5,400,258 A | 3/1995 | He | |
| 5,438,406 A | 8/1995 | Puschell | |
| 5,444,528 A | 8/1995 | Puschell | |
| 5,492,601 A | 2/1996 | Ostermayer et al. | |
| 5,541,413 A | 7/1996 | Pearson et al. | |
| 5,581,353 A | 12/1996 | Taylor | |
| 5,598,266 A | 1/1997 | Cornuejols | |
| 5,606,173 A | 2/1997 | Concannon et al. | |
| 5,642,189 A | 6/1997 | Alguard | |
| 5,642,192 A | 6/1997 | Gordon et al. | |
| 5,694,214 A | 12/1997 | Watanabe et al. | |
| 5,696,591 A | 12/1997 | Bilhorn et al. | |
| 5,714,763 A | 2/1998 | Chase et al. | |
| 5,774,213 A | 6/1998 | Trebino et al. | |
| 5,793,486 A | 8/1998 | Gordon et al. | |
| 5,795,394 A | 8/1998 | Belotserkovsky et al. | |
| 5,821,536 A | 10/1998 | Pettit | |
| 5,891,306 A | 4/1999 | Chase et al. | |
| 5,933,243 A | 8/1999 | Hagen | |
| 5,963,333 A | 10/1999 | Walowit et al. | |
| 5,992,318 A | 11/1999 | DiBello et al. | |
| 6,031,233 A | 2/2000 | Levin et al. | |
| 6,038,028 A | 3/2000 | Grann et al. | |
| 6,058,201 A | 5/2000 | Sikes et al. | |
| 6,074,483 A | 6/2000 | Belotserkovsky et al. | |
| 6,100,986 A | 8/2000 | Rydningen | |
| 6,111,649 A | 8/2000 | Tominaga et al. | |
| 6,262,419 B1 | 7/2001 | Huth-Fehre et al. | |
| 6,263,291 B1 | 7/2001 | Shakespeare et al. | |
| 6,272,440 B1 | 8/2001 | Shakespeare et al. | |
| 6,281,679 B1 | 8/2001 | King et al. | |
| 6,289,600 B1 | 9/2001 | Watts | |
| 6,297,879 B1 | 10/2001 | Yang et al. | |
| 6,327,374 B1 | 12/2001 | Piironen et al. | |
| 6,441,905 B1 | 8/2002 | Tojyo et al. | |
| 6,459,488 B1 | 10/2002 | Heffner | |
| 6,466,839 B1 | 10/2002 | Heaven et al. | |
| 6,476,920 B1 | 11/2002 | Scheiner et al. | |
| 6,494,446 B1 | 12/2002 | Tomiyama et al. | |
| 6,499,402 B1 | 12/2002 | Sikes et al. | |
| 6,515,746 B2 | 2/2003 | Opsal et al. | |
| 6,556,305 B1 | 4/2003 | Aziz et al. | |
| 6,556,306 B2 | 4/2003 | Jiang et al. | |
| 6,565,343 B1 | 5/2003 | Krycki | |
| 6,573,999 B1 | 6/2003 | Yang | |
| 6,584,435 B2 | 6/2003 | Mestha et al. | |
| 6,603,551 B2 | 8/2003 | Mestha et al. | |
| 6,639,201 B2 | 10/2003 | Almogy et al. | |
| 6,643,060 B2 | 11/2003 | Hashimoto et al. | |
| 6,646,752 B2 | 11/2003 | Chen et al. | |
| 6,690,357 B1 | 2/2004 | Dunton et al. | |
| 6,700,370 B2 | 3/2004 | Chen et al. | |
| 6,724,473 B2 | 4/2004 | Leong et al. | |
| 6,731,380 B2 | 5/2004 | Amara et al. | |
| 6,743,337 B1 | 6/2004 | Ischdonat | |
| 6,744,052 B1 | 6/2004 | Petersson et al. | |
| 6,757,069 B2 | 6/2004 | Bowles | |
| 6,760,103 B2 | 7/2004 | Shakespeare et al. | |
| 6,762,846 B1 | 7/2004 | Poris | |
| 6,763,322 B2 | 7/2004 | Potyrailo et al. | |
| 6,780,284 B2 | 8/2004 | Almi et al. | |
| 6,793,854 B1 | 9/2004 | Kirjavainen | |
| 6,805,899 B2 | 10/2004 | MacHattie et al. | |
| 6,816,636 B2 | 11/2004 | Cole et al. | |
| 6,822,785 B1 | 11/2004 | Chu et al. | |
| 6,849,844 B2 | 2/2005 | Khoury | |
| 6,856,436 B2 | 2/2005 | Brukilacchio et al. | |
| 6,949,734 B2 | 9/2005 | Neff et al. | |
| 7,259,853 B2 * | 8/2007 | Hubble et al. | 356/402 |
| 7,291,856 B2 | 11/2007 | Haran et al. | |
| 7,369,240 B1 | 5/2008 | Abbott et al. | |
| 2003/0007161 A1 | 1/2003 | Bowles | |
| 2003/0058441 A1 | 3/2003 | Shakespeare et al. | |
| 2004/0119781 A1 | 6/2004 | Szumla | |
| 2004/0124366 A1 | 7/2004 | Zeng et al. | |
| 2004/0212804 A1 | 10/2004 | Neff et al. | |
| 2004/0246493 A1 | 12/2004 | Kim et al. | |
| 2004/0260520 A1 | 12/2004 | Braendle et al. | |
| 2005/0065400 A1 | 3/2005 | Banik et al. | |
| 2005/0187478 A1 | 8/2005 | Beaudry et al. | |
| 2005/0236481 A1 * | 10/2005 | Gascoyne et al. | 235/454 |
| 2006/0028156 A1 * | 2/2006 | Jungwirth | 315/312 |
| 2006/0132777 A1 * | 6/2006 | Hubble et al. | 356/402 |
| 2006/0132796 A1 | 6/2006 | Haran | |
| 2006/0132808 A1 | 6/2006 | Jasinski et al. | |
| 2006/0164643 A1 | 7/2006 | Giakos | |
| 2006/0243931 A1 | 11/2006 | Haran et al. | |
| 2007/0139735 A1 | 6/2007 | Shakespeare et al. | |
| 2007/0144388 A1 | 6/2007 | Shakespeare et al. | |
| 2007/0153278 A1 | 7/2007 | Shakespeare et al. | |
| 2008/0157013 A1 | 7/2008 | Shakespeare | |

FOREIGN PATENT DOCUMENTS

| | | |
|---|---|---|
| DE | 19515499 A1 | 10/1996 |
| DE | 100 31 636 A1 | 1/2002 |
| EP | 0 319 158 A1 | 6/1989 |
| EP | 0 843 155 A1 | 5/1998 |
| EP | 1437222 A1 | 7/2004 |
| EP | 1457335 A1 | 9/2004 |
| EP | 1 491 877 A1 | 12/2004 |
| WO | WO 87/07381 A1 | 12/1987 |
| WO | WO 97/08537 A1 | 3/1997 |
| WO | WO 99/02941 A1 | 1/1999 |
| WO | WO 00/31521 A1 | 6/2000 |
| WO | WO 03/037111 A1 | 5/2003 |

| | | |
|---|---|---|
| WO | WO 2006/116672 A2 | 11/2006 |

OTHER PUBLICATIONS

Tarja Shakespeare et al., "Advanced Colour Control Through Reflectance Optimization", Proceedings 2nd EcoPaperTech Conference, Helsinki Finland, Jun. 1998, pp. 183-194.

Stokman et al., "Color Measurement by Imaging Spectrometry", Computer Vision & Image Understanding, San Diego, CA, US, vol. 79, No. 2, Aug. 2000, pp. 236-249.

Wandell, "Color Measurement and Discrimination", Journal of the Optical Society of America, USA. vol. 2, No. 1, Jan. 1985, pp. 62-71.

* cited by examiner

COLOR SENSOR

CROSS REFERENCE TO RELATED APPLICATIONS

This application claims the benefit of U.S. Provisional Patent Application No. 60/754,694, filed Dec. 29, 2005.

FIELD OF THE INVENTION

The present invention relates generally to measuring optical properties of a sample or of a material, and more particularly to measuring the color of a sample or of a material, and most particularly to measuring the color of a moving material in a manufacturing process.

BACKGROUND OF THE INVENTION

In the quality laboratory of a modern paper mill, color, brightness, whiteness, and fluorescence of the product are conventionally measured on a multiple sheet "pad" of paper, rather than on a single sheet. If only a single sheet is measured, the results will be influenced by both the partial transparency of the sheet and the reflectance of the backing against which the sheet is observed. Furthermore, the "infinite pad" value is usually what the end customer is concerned with, since this is typically how the customer will view the end product. However, these measurement conditions cannot necessarily be reproduced in-situ in the manufacturing process, where an "on-line" color sensor can view only a single thickness of the product.

Several strategies have been employed to improve the agreement of on-line color measurements with laboratory "pad" measurements. One strategy, an example of which is disclosed in U.S. Pat. No. 4,715,715, provides a backing to the sheet with an opaque material which approximates the color and optical scattering power of the paper being manufactured. A second strategy is to measure the sheet spectral reflectivity twice, once backed with a highly reflective (i.e., "white") material, and once backed with a highly absorptive (i.e., "black") material. From these independent measurements, the spectral transparency can be determined and the infinite pad spectral reflectivity calculated according to the Kubelka-Munk theory. An example of an apparatus for measuring dark and bright reflectances in succession is disclosed in U.S. Pat. No. 4,944,594.

The color of a material is commonly described using colorimetric quantities such as CIE L*a*b* values and auxiliary quantities such as Technical Association of the Pulp and Paper Industry (TAPPI) brightness. These can be computed from the total radiance factor of the material for a particular condition of illumination, together with knowledge of that illumination. For example, the reflective color or transmissive color of a material can be characterized using appropriate measurements of reflective or transmissive total radiance factor. To characterize color reliably, it may be necessary to know the total radiance factor in most or all of the visible range of wavelengths, at least from 420 nm to 650 nm, but typically from 400 nm to 700 nm. These measurements can be made using any particular geometry of illuminator and detector with respect to the measured material, and a number of geometries have been adopted as standards by international bodies.

For a non-fluorescent material, the reflective total radiance factor may always be identical to the reflectance spectrum, and the material's transmissive total radiance factor may always be equal to the material's transmittance. These are invariant under different conditions of illumination, so that a determination of reflectance or transmittance using a single illuminator is sufficient to characterize the corresponding total radiance factor under any other illuminator. Accordingly, it may only be necessary to use a single illuminator in measuring the color of a non-fluorescent material.

However, this may not be true for fluorescent materials, for which the measured total radiance factor generally depends on the illuminator used in the measurement. This is because the total radiance factor may be determined by fluorescent emission as well as by reflection or transmission of incident light. Thus, a total radiance factor measured using one illuminator need not be the same as the total radiance factor measured using a different illuminator, and a measured total radiance factor is generally valid only for the illuminator used in the measurement. For instance, in paper containing stilbene-based fluorescent whitening agents, the total radiance factor at 450 nm will depend on the ratio of the spectral power of the illuminator at 450 nm to the material's spectral power in the excitation band for fluorescent emission at 450 nm, particularly from 330 nm to 420 nm. This issue and the consequences for color measurement are explained in more detail in T. Shakespeare & J. Shakespeare "Problems in colour measurement of fluorescent paper grades", Analytica Chimica Acta 380(2)227-242, 1999.

A strategy used to measure the color of fluorescent paper is to measure the total radiance factor (which in prior art is sometimes misleadingly referred to as a reflectance factor) using two different illuminators. For example, U.S. Pat. No. 4,699,510 discloses an on-line color sensor for measuring the color of a moving sheet of paper that contains fluorescent whitening agents (FWA). Fluorescent whitening agents typically absorb the violet and ultraviolet energies of incident light and re-emit these energies in the blue range of the visible spectrum to give the paper a whiter appearance. The '510 patent discloses techniques for determining the color spectrum of such treated paper if illuminated by a defined source such as the CIE D65 (North Sky Daylight) standard source. The D65 standard source has an energy distribution which, compared to other standard sources such as CIE source C, is relatively bright in the 300-400 nm range; consequently, paper with fluorescent whitening agents is likely to appear bluer if illuminated by a D65 source.

The color sensor of the '510 patent has two sources of illumination, one an ultraviolet source which emits light primarily in the excitation band of fluorescent whitening agents, the other a visible light source with an emission spectrum approximating a CIE standard source which also emits a significant amount of light in the UV or excitation range of FWA.

However, methods such as those of the '510 patent may be of limited efficacy, in that by using two illuminators, it is possible to reliably determine the total radiance factor only for the range of illuminators which can be formed as linear combinations of the two illuminators used in measurement. An alternative set of methods is disclosed in U.S. Pat. No. 6,263,291 and U.S. Pat. No. 6,272,440 which describe sequential use of plural monochrome or narrow-band illuminators in measurement of color. In this way, the measurement apparatus sequentially determines individual rows of the radiance transfer factor matrix, from which a total radiance factor can be computed for any illuminator. However, these are slow methods of limited reliability, since the devices require extended sequences of measurements with long integration times in each measurement of the sequence, and the devices also demand precise measurements of near-zero light fluxes to characterize the off-diagonal values of the radiance transfer factor matrix. The devices may thus be poorly suited to industrial applications, which may require prompt measurement of single samples, or may require measurement of rapidly moving materials whose color may be varying. For example, in manufacture of paper, the paper sheet may move at speeds approaching 30 meters per second, and exhibit variations in color properties over distances of less than one meter.

An improved approach is disclosed in U.S. patent application Ser. No. 09/957,085 in which plural rich spectral illuminator states are used sequentially, possibly in a random sequence, and a statistical decomposition of spectrophotometric measurements is used to infer the radiance transfer factor matrix. In this approach, an intrinsically unstable light source, such as a Xenon flash tube or some other light source with an unstable power supply is used to ensure spectral variability of the illuminator. Thus, the radiance transfer factor matrix can be determined from a sequence of measurements, but the method does not require long measurement integrations in each measurement nor does the method require particularly precise measurements of small light fluxes. However, the method does require that the entire radiance transfer factor matrix be known from a sequence of measurements in order to compute the total radiance factor for a specific illuminator. This is because it is unlikely that any particular illuminator state used in measurement matches the specified illuminator closely enough for a single measurement to reliably provide its total radiance factor. The method therefore requires a significant time in which to determine the radiance transfer factor, during which time the sample to be measured must be stationary, or if measurement is made of a moving material, the properties of the material must not change over the distance moved during the determination.

In paper and board manufacturing, various machines impart vibration to the environment. These vibrations may shorten the expected life of the illuminating device used in the previously described sensor and similar devices. A short life of the illuminating device may require replacement of the illuminating device which not only incurs costs for replacement but may also incur costs associated with a component of the manufacturing process going off-line while the illuminating device is replaced. In particular, filament-based illuminators such as Tungsten-halogen lamps may be prone to rapid failure in vibration-rich environments, since the filament is fragile and easily disintegrates. Low-pressure discharge tubes, such as Xenon flashtubes, also suffer from shortened service life in such environments, due to the existence of stress concentration points in the bulb material and the likelihood of resonant vibration frequencies.

Accordingly, an efficient and effective device, method, and system are needed for rapid and timely determination of the color of fluorescent and non-fluorescent samples and materials. In addition, the device, system and method may provide an illuminating device that can handle unstable environments with substantial vibration. The device, system and method may provide an illuminating device that provides for efficient measurement of the color of fluorescent material and maintenance of the sensor.

SUMMARY OF THE INVENTION

It is, therefore, an object of the present invention to provide devices, systems, and methods for measuring the color of a sample or of a material. According to an exemplary embodiment of the present invention, the device may have at least one light emitting diode for directing a beam of ultraviolet light onto the sample and a means for controlling the operation of said light emitting diode. The device may also have at least one light detector for receiving the beam of light reflected from or transmitted through the sample and measuring at least one wavelength band of the received light. The device may further have a measurement analyzer for determining the color of the sample based on the measured light.

According to an exemplary embodiment of the present invention, the device may incorporate the following embodiments. In one embodiment, the light emitting diode may direct a beam of ultraviolet light and a beam of visible light onto the sample. In another embodiment the device may have a second light emitting diode for directing a beam of visible light onto the sample. In another embodiment the device may have a light emitting diode controller for causing the light emitting diode to continuously emit light at about the three hundred to about the eight hundred nanometer wavelength and intermittently emit light at bands within about the three hundred to about the eight hundred nanometer wavelength. In another embodiment, the light emitting diode control may regulate the light emitting diode by altering an input voltage, an input current, an input pulse width, and an operating temperature. Each light emitting diode may be located on a separate circuit board. At least one continuous light emitting diode may be located on a first circuit board and at least one intermittent light emitting diode may be located on a second board. In yet another embodiment, the device may have a micro optic device for focusing and reflecting the beam of light from the at least one light emitting diode onto the sample. In another embodiment, plural light emitting diodes may be regulated so as to provide an aggregate light beam which matches that of a specified illuminator. In a variant of this embodiment, plural light emitting diodes may be regulated so as to provide a sequence of illumination states, not all of which may be the same, each state providing an aggregate light beam matching that of a specified illuminator. In yet another variant of this embodiment, plural light emitting diodes may be regulated so as to provide a sequence of illumination states, not all of which may be the same, each state providing an aggregate light beam which is a perturbation of a specified illuminator, but none of which needs to exactly match the specified illuminator. In yet another embodiment, the measurement analyzer may estimate the color of the sample under a specified illuminator which may not necessarily be the same as any illuminator used in the measurement.

BRIEF DESCRIPTION OF THE DRAWINGS

The above and other objectives and advantages of the present invention will be apparent upon consideration of the following detailed description, taken in conjunction with the accompanying drawings, in which like reference numbers refer to like parts throughout, and in which.

DETAILED DESCRIPTION OF THE INVENTION

Figure 1:
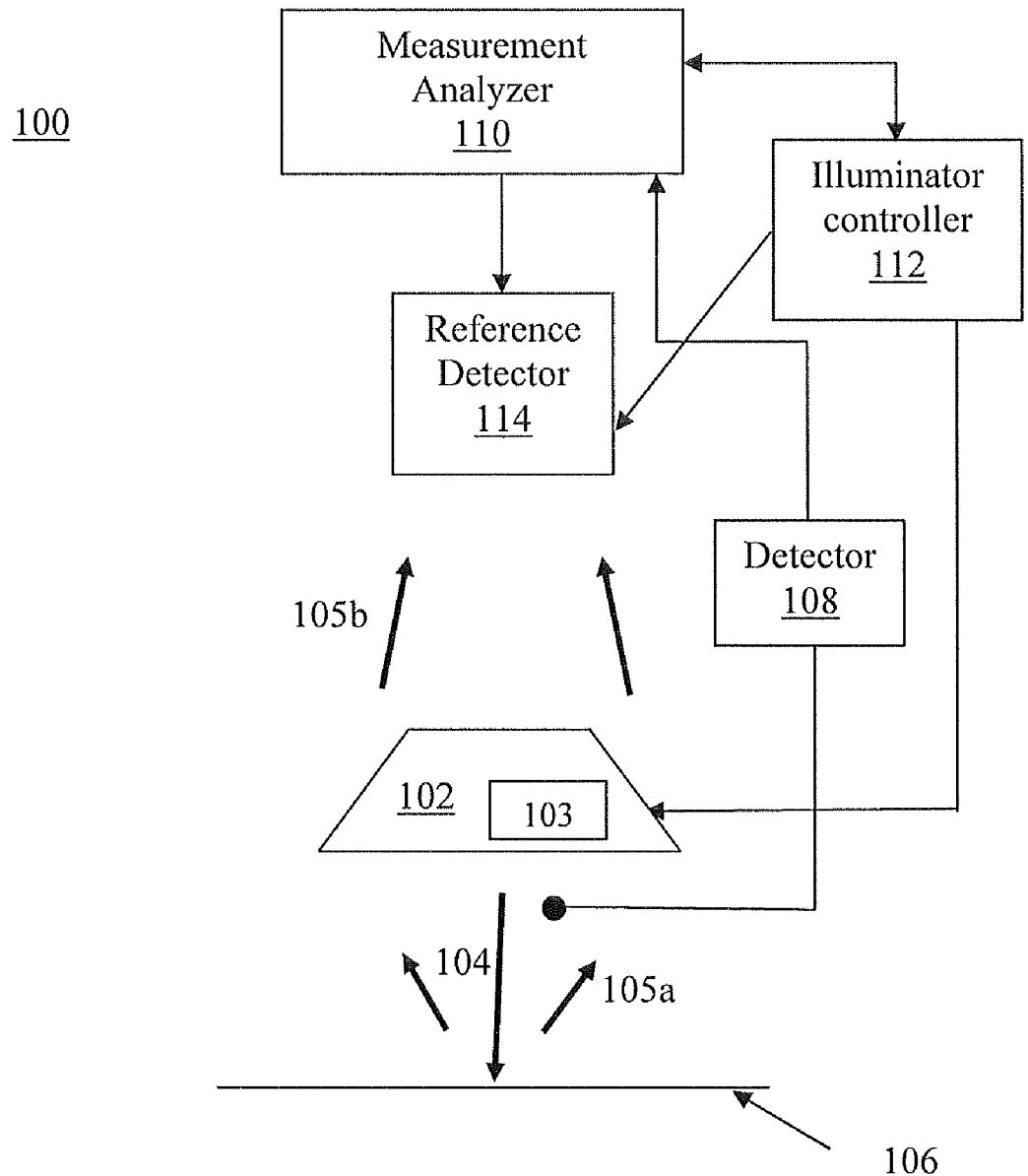
FIG. 1 is a generalized schematic of an illuminating device used to implement a first exemplary light source embodiment of the present invention.

A color sensor may determine the color of a sample by directing a beam of light at the sample to illuminate the sample and by detecting and measuring the light that has interacted with the sample. The interaction of the light with the sample may include absorption, scattering and excitation of fluorescent emission. The detection of light which has interacted with the sample may be on the same side of the sample as the illumination, or may be on the opposite side to the illumination, or may be performed on both sides simultaneously or sequentially. The color sensor may use a measurement analyzer to determine the color of the sample based on the measured light. The illumination of the sample may employ one or more light emitting diodes. The color of the sample may be determined for an infinitely thick opaque pad formed of like samples, or for the sample with a backing material of specified properties.

The light emitting diodes may be regulated so as to produce one or more illumination states for the measurement. The color of the sample may be determined for an illuminator which matches an illumination state used in the measurement. The color of the sample may be determined for an illuminator which does not match any illumination state used in the measurement, but which may be expressed as a linear combination of illumination states used in the measurement. The color of the sample may also be determined for a specified illuminator which does not match any illumination state used in the measurement and which is not expressible exactly as a linear combination of illumination states used in the measurement; in this case, the color can be determined as belonging to an interval of colors which are defined by a set of linear combinations of illumination states used in the measurement, this set forming a set of perturbations approximating the specified illuminator.

The color sensor comprises at least one illuminating device, at least one measurement detector, at least one illuminator controller, and a measurement analyzer. It may also comprise at least one reference detector. The measurement analyzer can be separate from all the other components, which are collectively termed the measurement device. The measurement analyzer is not limited just to reflectance measurements of color. The measurement analyzer can be modified to also measure transmittance measurements of color or even both characteristics simultaneously. The measurement analyzer can be separate from all the other components, which are collectively termed the measurement device.

The measurement detector and the reference detector are preferably spectrometers. A spectrometer comprises a spectrograph (containing a light entrance port and a dispersive element such as a grating) and a detector, for example, a linear CCD detector with 128 to 2048 photodiodes. Instead of a grating, the dispersive element may be a linear variable filter or a set of discrete optical filters of known characteristics. The spectrometer may have additional optical elements such as mirrors or beam splitters to direct the beam towards the dispersive element, or to distribute the beam across the sample of the dispersive element, or to focus dispersed light onto a detector. The detector may be a two-dimensional array of photodiodes instead of a linear array, or it may be a set of discrete photodetectors.

One function of a spectrometer is to isolate an approximately collimated portion of a radiance with the entrance port; to disperse this entered light beam into plural wavelength bands using the dispersive element; to distribute the dispersed light onto the detector, such that specific wavelength bands are incident onto specific positions in the detector; to detect and quantify the light falling on plural positions in the detector; and/or to produce spectral measurements from which colorimetric data may be derived. The spectrometer may be replaced by a spectrocolorimeter, which can produce as output only colorimetric data (such as tristimulus values and derived colorimetric data such as brightness). However, use of a spectrocolorimeter may result in reduced reliability of the measurement and reduced efficacy in measurement of fluorescence.

The measurement device may have a measurement detector. The measurement detector may be a spectrometer which measures the spectrum of the irradiance from the sample. The measured light is light from the light source(s) which has illuminated the sample and interacted with the sample by being transmitted through or reflected from the sample, and includes fluorescent emission or phosphorescent emission from the sample in response to the illumination.

The measurement device may also have a reference detector. The reference detector may be a spectrometer which measures the spectrum of the irradiance from the light source(s). The measured light has not interacted with the specimen to be measured or with a calibration standard. The reference spectrometer's input may be obtained as a portion of the light produced by the light source(s).

Referring to FIG. 1, sensor 100 may include illuminating device 102 for providing a light beam 104 to illuminate a sample 106 at a pass-line. The illuminating device 102 provides a focused beam of light or collimated light beam, for example by utilizing one or more light emitting diodes. The reflected beam of light 105a is detected by detector 108. The detector 108 supplies the measured values of light to a measurement analyzer 110. A portion 105b of the light produced by the illuminating device 102 may be directed to reference detector 114. The reference detector 114 supplies the measured values of light to the measurement analyzer 110. The measurement analyzer 110 uses the values of light from the detector 108 to determine the color of the sample 106 and may additionally use values of light from the reference detector 114 to determine the color of the sample 106. The measurement analyzer 110 may also regulate an illuminator controller 112. The measurement analyzer 110 may direct the illuminator controller 112 to cause the illuminating device 102 to emit light in different relative intensities at each of plural wavelength bands. The embodiments of the invention are not limited by a reference detector. The various embodiments may be implemented without a reference detector as would be appreciated by one skilled in the art.

The illuminating device 102 may be one or more Light Emitting Diodes (LEDs). The LEDs may emit light at various wavelengths. The LEDs may emit light in a continuous or an intermittent manner. Altering the current and/or voltage used to drive a LED may also influence the relative spectral power distribution of light emitted by the LED. The illuminating device 102 may also use several different light emitting diodes that emit light having different spectrums. The sample sensor 100 may control when the individual light emitting diodes are illuminated thereby controlling the wavelength spectrum of light emitted by the illuminating device 102. The LEDs may be large surface area LEDs produced by an array of miniature LEDs in a honeycomb structure. The LEDs may also be individually controlled wavelength bands, for example, R-G-B LEDs. The LEDs may also be broadband emitters, such as those constructed using multiple phosphors or incorporating quantum dots.

The illuminating device 102 may comprise heat sink panels, optical elements 103, one or more circuit boards on which LEDs are mounted, and mechanical arrangements for mounting the device. Provision can be made for replacement of part or all of an illuminating device at regular intervals or when diagnostic tests indicate degraded performance. Optical elements 103 may include beam shaping optics, such as microlenses or micro-reflectors or diffusers, spectral filters, and so forth. Different illuminating devices may have different LED types/combinations. The optical element 103 may, for example, modify at least one characteristic of the light emitted by the illuminating device 102. The modified characteristic(s) could include the spatial intensity distribution of the light, the spectral power distribution of the light, or the state of polarization of the light.

The irradiance incident on the reference detector 114 may have essentially the same spectral power distribution as the irradiance incident on the sample. Preferably, the irradiance produced by the illuminator(s) is divided between these two purposes using one or more of the optical elements 103, but need not be divided in equal amounts. For instance, some optical fibers or mirrors or achroic beam splitters may cause a portion of the light from one or more light source(s) to be directed to the reference detector and another portion to be directed to illuminate the sample. Alternatively, a multi-ported integrating sphere, the internal surface of which is diffusely reflective, may be used to combine irradiance from one or more light source(s), and to supply a specific fraction of the combined irradiance to a reference detector and to supply another portion of the combined irradiance to illuminate a sample. Instead of a sphere, a partial sphere or other suitable shape may be used, and the number and positions of light entry ports and light exit ports can be chosen.

The measurement geometry is the geometric arrangement relative to the sample of the irradiance incident on the sample and the irradiance from the sample incident on the measurement detector. There are numerous measurement geometries in common use, and some have been formalized in international standards, including 0/45, 45/0, 0/d, d/0 and so forth. The first number in each dyad is the angle in degrees relative to the sample at which the sample is to be illuminated, while the second number is the angle in degrees relative to the sample at which irradiance from the sample is to be measured. By convention, the 0° angle in these dyads is taken to be perpendicular to the sample being illuminated. The designation "d" instead of a numeric angle indicates that the illumination or measurement is to be diffuse or nondirectional. Moreover, for directional illumination at angles greater than 0°, the illumination may be from a single azimuth direction, from plural azimuth directions, or from a circular annulus.

The portion of the sample from which irradiance is directed to the measurement detector is termed the viewed area. The viewed area is preferably a circular disk of radius 10 mm, but may be larger or smaller, and need not be circular or contiguous. The illuminated portion of the sample may include at least the entire viewed area, and preferably includes an additional area bounding the viewed area. The illumination is preferably spatially uniform over at least the viewed area, both in intensity and in spectral power distribution at any measurement instant.

The illuminator controller 112 may be passive to the measurement analyzer 112, or may be an autonomous unit. The illuminator controller 112 controls the light output from the illuminating device 102 or a LED or group of LEDs by controlling the voltage or current supplied to the LED or group of LEDs. The illuminator device 102 may be operated in a continuously-on mode, or in a flashing on-off mode. In the continuously-on mode, the power used for an illuminator may be fixed, or may be varied as a function of time, either according to a deterministic schedule or in a random or pseudo-random sequence. In the continuously-on mode, an illuminator may also be intermittently switched off. In the flashing on-off mode, the power used for an illuminator may be fixed, or may be varied from flash to flash, either according to a deterministic schedule or in a random or pseudo-random sequence. The operating mode, voltage, current, power, timing and so forth need not necessarily be the same for all LEDs.

In an exemplary case, an autonomous illuminator controller operates the LEDs in a fixed sequence of states, each of a specified duration, where in each state a voltage or current or power is defined for each LED or group of LEDs and a timing is defined for switching the LED or group of LEDs on and off. For instance; in a first state lasting 10 milliseconds a first LED may be continuously on with a current of 200 milliamps, a second LED may be flashing on-off at 1000 Hz with a flash current of 2 amps and a flash duration of 100 microseconds, and a third LED may be continuously on with current rising linearly from 100 milliamps to 300 milliamps; while in a second state lasting 5 milliseconds the first and second LEDs are both continuously on and each has a current of 150 milliamps, and the third LED is switched off.

The illuminator controller 112 may also perform thermal management of the LEDs, such as by monitoring their temperatures and by operating heating or cooling devices to keep their temperatures within acceptable limits. For example, a simple way to heat the LEDs is to switch them on at times when measurements are not being made.

The sample 106 may be a variety of materials handled in a manufacturing process or mechanized process. For example, the sample 106 may be a web of paper or board, or a sheet or film of plastic, or a woven or nonwoven fabric. The web is continuously moved throughout the manufacturing process using various rollers, presses, and other machinery. The various embodiments of the sample sensor described herein may comply with various known standards, for example, those of the Technical Association of the Pulp and Paper Industry (TAPPI) standards as well as other known industry and government standards. Sample 106 is not limited to a web of paper. Sample 106 may be individual sheets of material that are advanced on a conveyor belt or other devices for transporting sheets of material.

The sample 106 can be transparent, translucent or opaque. For a translucent sample, reflectance measurements with black and white backing can be utilized with the Kubelka-Munk method to estimate true reflectance for an infinitely thick pad formed of the specimen. The Kubelka-Munk method can also be extended to accommodate fluorescence in this estimation. A calibration tile is typically an opaque white tile with high reflectivity at all wavelengths of interest. During calibration, a calibration tile is typically placed in the same position in which the sample to be measured is normally located. However, this is not a necessity if the optical path is folded or compensated by other means. Then calibration tiles can be located even "inside" the instrument, in a position which is optically equivalent to the specimen position.

Light beam 104 is reflected off the sample 106. The intensity of the reflected light is measured with light detectors 108. The light detectors 108 may use optic fiber or other micro optics to collect the light to be detected by the light detectors 108. The light detectors convert collected light into an electrical charge. The light detectors 108 may be composed of a variety of devices, for example, Charge Coupled Devices (CCD), digital Complementary Metal Oxide Semiconductor (CMOS) photodiode arrays, discrete photodiodes, or any other suitable light sensitive device. The signal generated by light detectors 108 may be analog or converted to a digital signal for processing. The signal of light detectors 108 is fed into a measurement analyzer 110.

A reference detector 114 may be used to provide a reference point for the measurement analyzer 110. The reference detector 114 may be positioned to receive an accurate sample of the light emitted by the illuminating device 102. According to the first exemplary embodiment, the reference detector may use an optical fiber to gather light directly from the illuminating device 102 or from the edges. The optical fiber may prevent reflected light from corrupting the reference light sample collected by the reference detector 114. The reference detector may have a similar light detecting structure as previously discussed with regard to the light detectors 108.

The measurement analyzer 110 may compare the intensity and spectrum of the light received from light detectors 108 and reference detectors 114 with known values of intensity for at least one calibration tile of known properties. By illuminating at least one calibration tile and measuring the light at both the reference detector and the measurement detector, it is possible to form a relation between the photometric scales of the two detectors. In the simplest case, a normalizing ratio for the detectors can be determined for each spectral band. Thereafter, in measuring a sample 102, the relation between these photometric scales can be used to obtain a total radiance factor measurement from the light measurements at the two detectors.

Architecturally in terms of hardware, the measurement analyzer 110 may include a processor, memory, and one or more input and output interface devices. The local interface may have additional elements, which are omitted for simplicity, such as controllers, buffers (caches), drivers, repeaters, and receivers, to enable communications. Further, the local interface may include address, control, and/or data connections to enable appropriate communications among the components of a network.

The measurement analyzer 110 may determine the characteristics of the sample 106 by determining the ratio of the reflecting light beam intensity and/or spectrum to the intensity of the illuminating light beam from the illuminating device 102. After compensating for the relation between photometric scales, the ratio of the light measured at the measurement detector to the light measured at the reference detector is the total radiance factor of the sample 106 for the illuminator used for that measurement. The measurement analyzer 110 may use a stored table, equations, or a combination thereof to compute the measurement characteristics of the sample 106.

The systems and methods may also be incorporated in software used with a computer or other suitable operating device of the measurement analyzer 110. Measurement analyzer 110 may also include a Graphic User Interface (GUI) to allow the administrator or user to enter, view and store the characteristics or enter constraints associated with the desired characteristics to control other devices of the manufacturing process.

Figure 2:
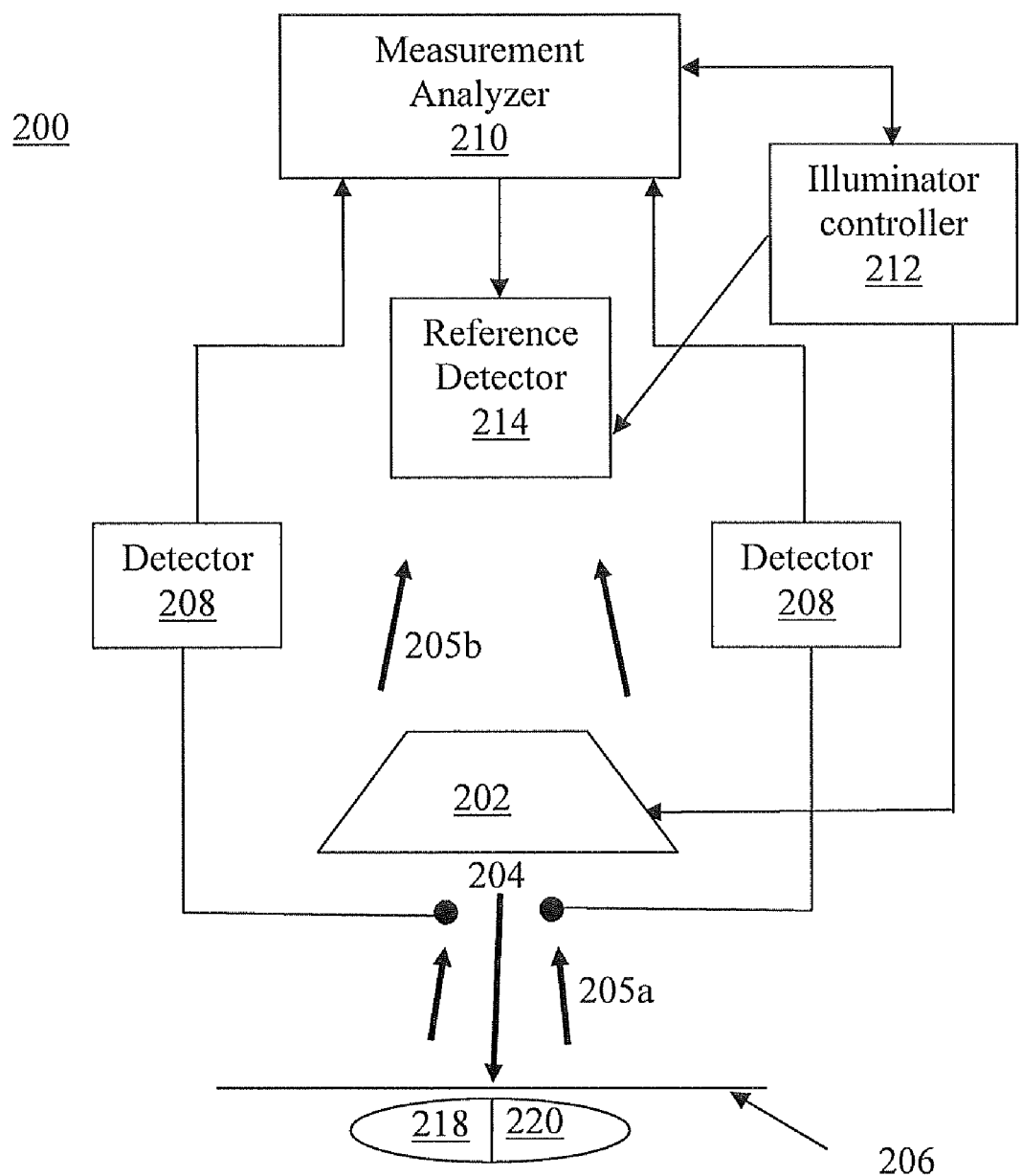
FIG. 2 is a generalized schematic of an illuminating device used to implement a second exemplary light source embodiment of the present invention.

Referring to FIG. 2, sensor 200 may include illuminating device 202 for providing a light beam 204 to illuminate a sample 206 at a pass-dine. The illuminating device 202 provides a focused beam of light or collimated light beam, for example by utilizing one or more light emitting diodes. The reflected beams of light 205a are detected by detectors 208. The detectors 208 supply the measured values of light to a measurement analyzer 210. The measurement analyzer 210 uses the values of light to determine the characteristics of the sample 206. The measurement analyzer 210 may also regulate an illuminator controller 212. The measurement analyzer 210 may direct the illuminator controller 212 to cause the illuminating device 202 to emit different wavelengths or intensity of light. The components of sample sensor 200 may incorporate aspects as previously described in sample sensor 100.

A reference detector 214 may be used to provide a reference point for the measurement analyzer 210. The reference detector 214 may be positioned to receive an accurate sample of the light emitted by illuminating device 202. According to the second exemplary embodiment, the reference detector 210 may use a trapezoid mirror and/or other micro lens and optical components to gather light 205b directly from the illuminating device 202 or from the edges. The trapezoid mirror may prevent reflected light from corrupting the reference. According to the second exemplary embodiment the light sample collected by the detectors 208 may be reflected onto the sample 206 with a first background 218 and a second background 220. The backgrounds 218, 220 may allow the measurement analyzer to determine additional characteristics of the sample 206 based on the reflected light between the contrasting backgrounds 218, 220. In one example, the first background 218 may be black and the second background may be white 220.

Figure 3:
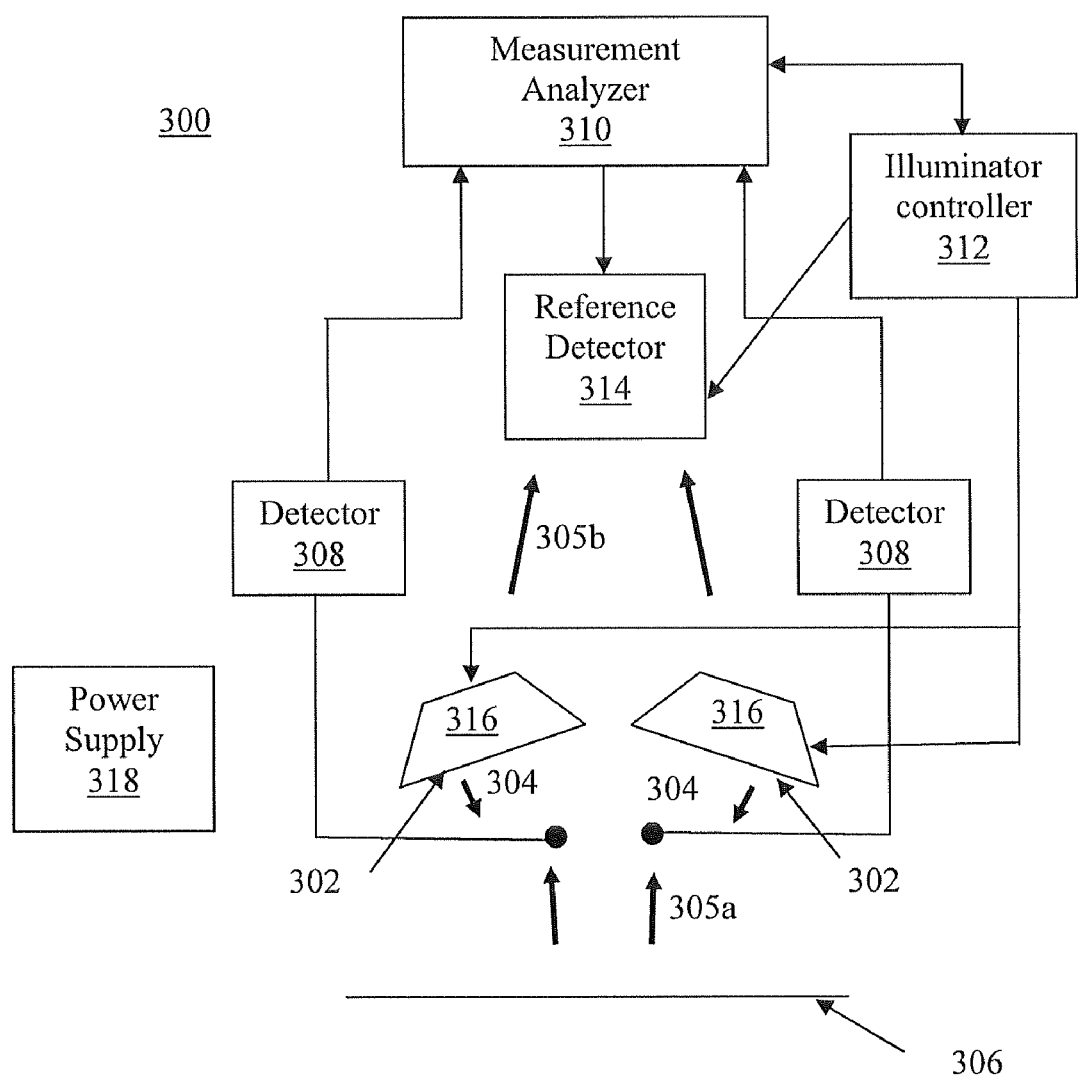
FIG. 3 is a generalized schematic of an illuminating device used to implement a third exemplary light source embodiment of the present invention.

Referring to FIG. 3, sensor 300 may include illuminating device 302 for providing a light beam 304 to illuminate a sample 306 at a pass-line. The illuminating device 302 provides a focused beam of light or collimated light beam, for example by utilizing one or more light emitting diodes. According to the third exemplary embodiment the LEDs may be located on two or more circuit boards 316. The circuit boards 316 may comprise LEDs that emit different spectrums of wavelengths. For example, one circuit board may include LEDs that emit light in the visible spectrum of light. The circuit boards 316 may emit light from different directions. The second circuit board may include LEDs that emit light in the ultraviolet spectrum of light. The circuit boards 316 may make it possible to replace LEDs without requiring all LEDs of the sensor to be replaced at the same time. According to the above example, an administrator may replace the ultraviolet LEDs on a more regular interval. One or more power supplies 318 provide power via the circuit boards 316 to the illuminating devices 302.

The reflected beams of light 305a are detected by detectors 308. The detectors 308 supply the measured values of light to a measurement analyzer 310. The measurement analyzer 310 uses the values of detected light to determine the characteristics of the sample 306. The measurement analyzer 310 may also regulate an illuminator controller 312. The measurement analyzer 310 may direct the illuminator controller 312 to cause the illuminating device 302 to emit light in different relative intensities at each of plural wavelength bands. The components of sample sensor 300 may incorporate aspects as previously described in sample sensor 100.

A reference detector 314 may be used to provide a reference point for the measurement analyzer 310. The reference detector 314 may be positioned to receive an accurate sample of the light emitted by illuminating device 302. According to the third exemplary embodiment the reference detector 314 may detect light 305b at a location between the two circuit boards 316 to gather light directly from the illuminating device 302.

Figure 4:
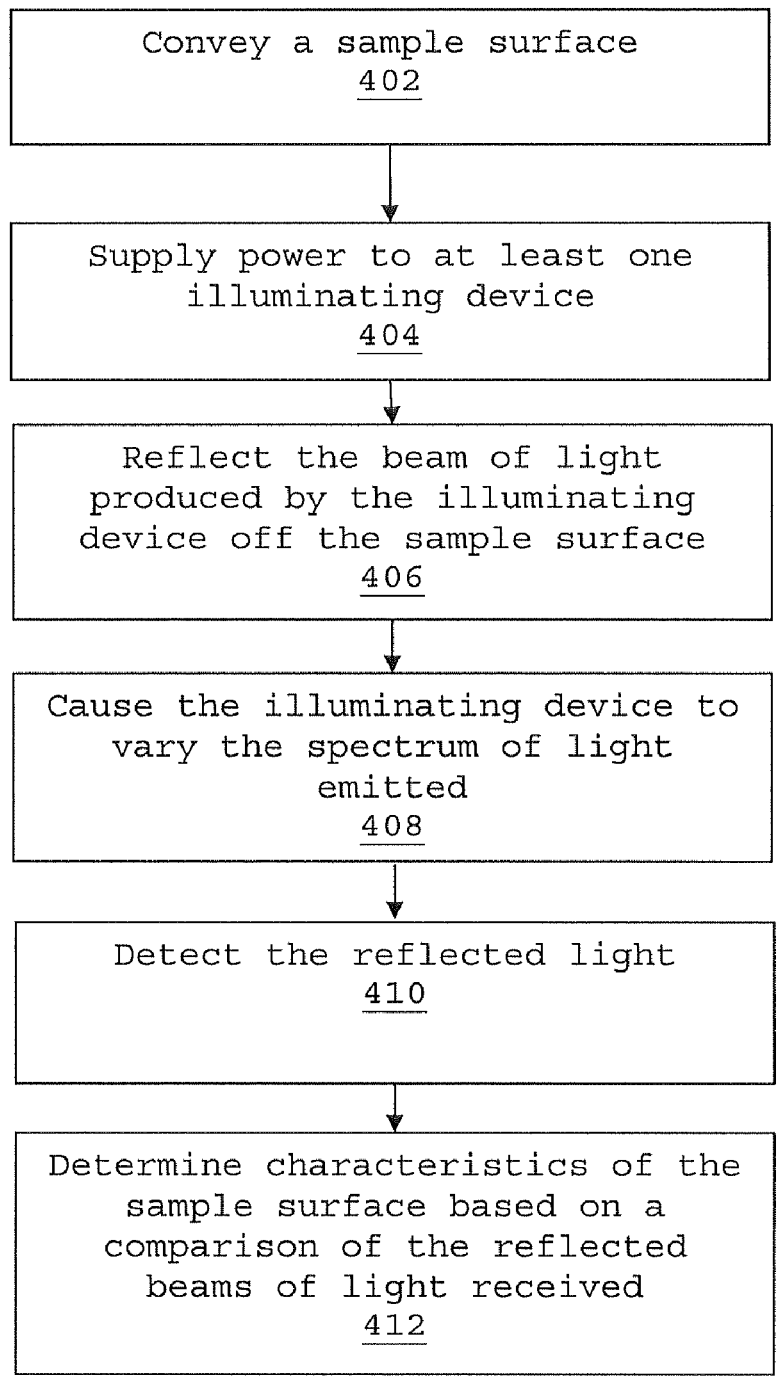
FIG. 4 is a flow chart illustrating a first exemplary method for the sensor used to implement the illuminating device embodiment of the present invention.

FIG. 4 is a flow chart illustrating a first exemplary method for the sensor used to implement the illuminating device embodiment 400 of the present invention. There are two phases to the method, a calibration phase depicted above the dashed line, in which parameters of the illuminating device are determined, and an operation phase depicted below the dashed line, in which the device is used to measure a sample.

In the calibration phase, an initial power setting is selected (block 402). Power with this setting is supplied to the illuminating device, causing it to produce a first beam of light (block 404). The first beam of light thus produced is directed onto a reference material of known properties (block 406). A reference material may be, for example, a diffusely reflecting material of known high reflectance through at least the visible range. A reference material may also be a fluorescent material of known fluorescence characteristics and also of known reflectance in the excitation and emission bands of its fluorescence. A second beam of light which has interacted with a reference material is received (block 408), and the spectral power distribution of the received second beam is measured (block 410). The spectral power distribution of the first beam of light is determined from the measured spectral power distribution of the second beam of light and the known properties of the reference material (block 412). The power setting and the determined spectral power distribution of the first beam of light are stored (block 414). The power setting is modulated so as to alter the spectral power distribution of the first beam of light (block 416). Power with the new settings is then supplied to the illuminating device, causing it to produce a first beam of light (block 404). The sequence of blocks 404, 406, 408, 410, 412, 414, and 416 is repeated a number of times, such that a variety of power settings and corresponding spectral power distributions are stored. The sequence may be repeated using each of plural reference materials, such as reference materials having different fluorescence characteristics.

The operation phase can be used after the calibration phase has been performed at least once. In the operation phase, a desired spectral power distribution for illumination is specified (block 452). From the stored power settings and stored spectral power distributions obtained in the calibration phase, a power setting is determined which will cause the illuminator to produce light of the desired spectral power distribution (block 454). The manufacturing process advances sample 106 to the pass-line of sensor 100 (block 456). Illuminator controller 112 supplies power with the determined settings to the illuminating device 102 causing it to produce a first beam of light of the desired spectral power distribution (block 458). This may be accomplished by supplying power to selected LEDs of the illuminating device 102. Illuminating device 102 directs the first beam of light 104 onto sample 106 (block 460). The beam of light 104 interacts with sample 106 producing a second beam of light which is received by detector 108 (block 462). The detector 108 measure the spectral power distribution of the received second beam of light (block 464). The measurement analyzer 110 determines the characteristics of sample 106 from the spectral power distribution of the received light (block 466). The measurement analyzer may change the desired spectral power distribution for illumination during operation, and may employ measurements made by illuminating a sample with a single spectral power distribution or with each of two or more spectral power distributions in determining characteristics of the sample. The calibration phase may be repeated from time to time, so that the effects of component aging can be compensated and performance degradation can be avoided. One or more suitable reference materials may be contained within the measurement apparatus, with mechanisms which either deploy it into the measurement position, or equivalently alter the light path of the first and second light beams so that the calibration can be performed with minimal disturbance to normal operation.

Figure 5:
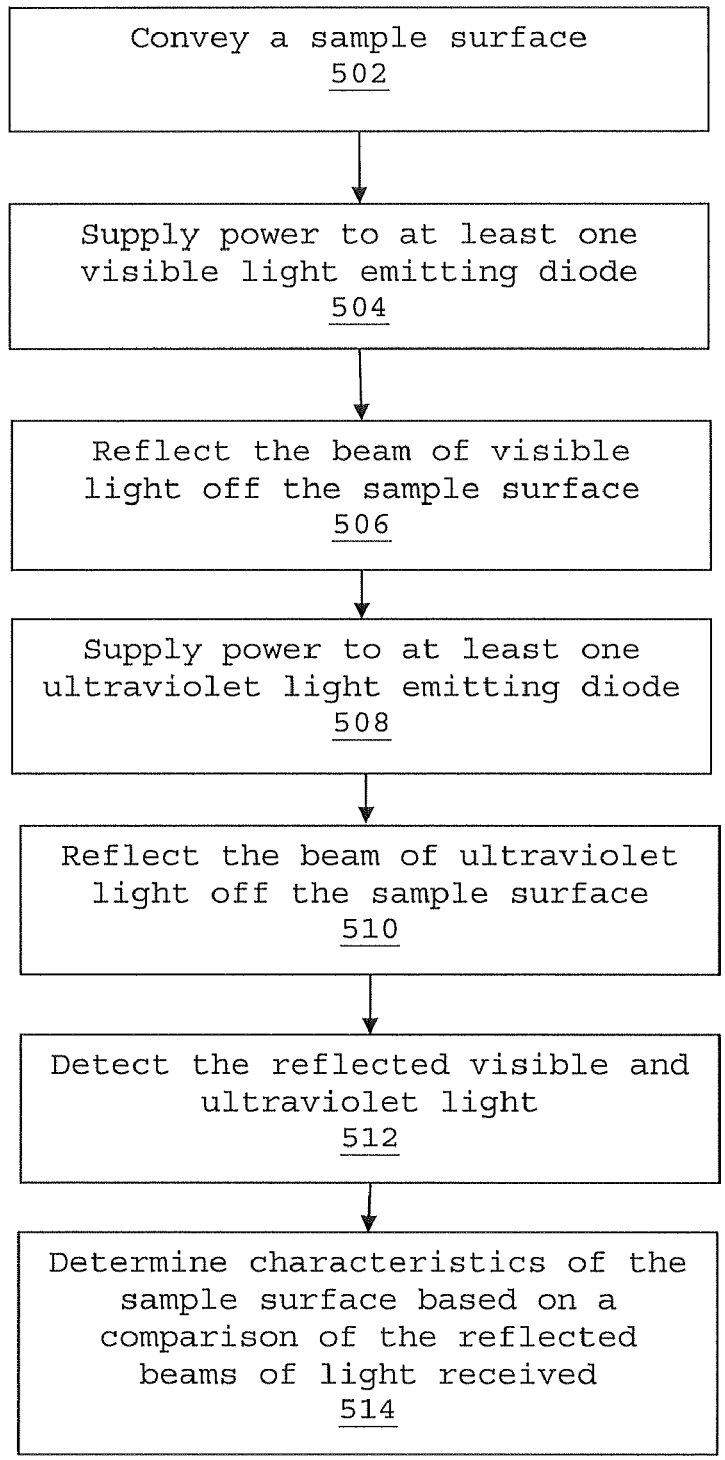
FIG. 5 is a flow chart illustrating a second exemplary method for the illuminating device embodiment of the present invention.

FIG. 5 is a flow chart illustrating a second exemplary method for the illuminating device embodiment 500 of the present invention. The manufacturing process advances sample 106 to the pass-line of sensor 100 (block 502). A desired spectral power distribution for illumination is selected (block 504). An initial power setting for the illuminators is selected (block 506). Illuminator controller 112 supplies power with the given power setting to the LEDs of illuminating device 102 causing it to produce a beam of light (block 508). The beam of light thus produced is divided into a first beam and a second beam (block 510). The first beam and the second beam need not have the same total power, but their relative spectral power distributions are the same at least in the visible range. The second beam of light is directed onto a reference detector 114 (block 512). The reference detector 114 measures the spectral power distribution of the second beam as a reference spectral power distribution (block 514). The illuminator controller 112 modulates the power setting of the LEDs so as to minimize the difference between the measured reference spectral power distribution and the desired spectral power distribution (block 516). The sequence of blocks 508, 510, 512, 514, 516 is repeated until the difference between the measured reference spectral power distribution and the desired spectral power distribution is sufficiently small. The sequence is repeated also whenever the illuminator controller selects a different desired spectral power distribution for illumination. The sequence may also be repeated from time to time during operation to ensure that the spectral power distribution used for illumination does not deviate from the desired spectral power distribution.

The first beam of light is directed onto the sample 106 (block 518). A third beam of light, which has interacted with the sample, is received by detector 108 (block 520). The detector 108 measures the spectral power distribution of the received third light beam as a measured spectral power distribution (block 522). When the reference spectral power distribution is sufficiently close to the desired spectral power distribution, the characteristics of the sample can be determined from the measured spectral power distribution by the measurement analyzer 110 (block 524). The measurement analyzer 110 may change the desired spectral power distribution for illumination during operation, and may employ measurements made by illuminating a sample with a single desired spectral power distribution or with each of two or more desired spectral power distributions in determining characteristics of the sample. The power setting which minimizes the difference between the reference spectral power distribution and the desired spectral power distribution can be stored by the measurement analyzer or by the illuminator controller. A stored power setting for a desired spectral power distribution can be used as an initial power setting if the measurement analyzer selects the same desired spectral power distribution at a future time.

Figure 6:
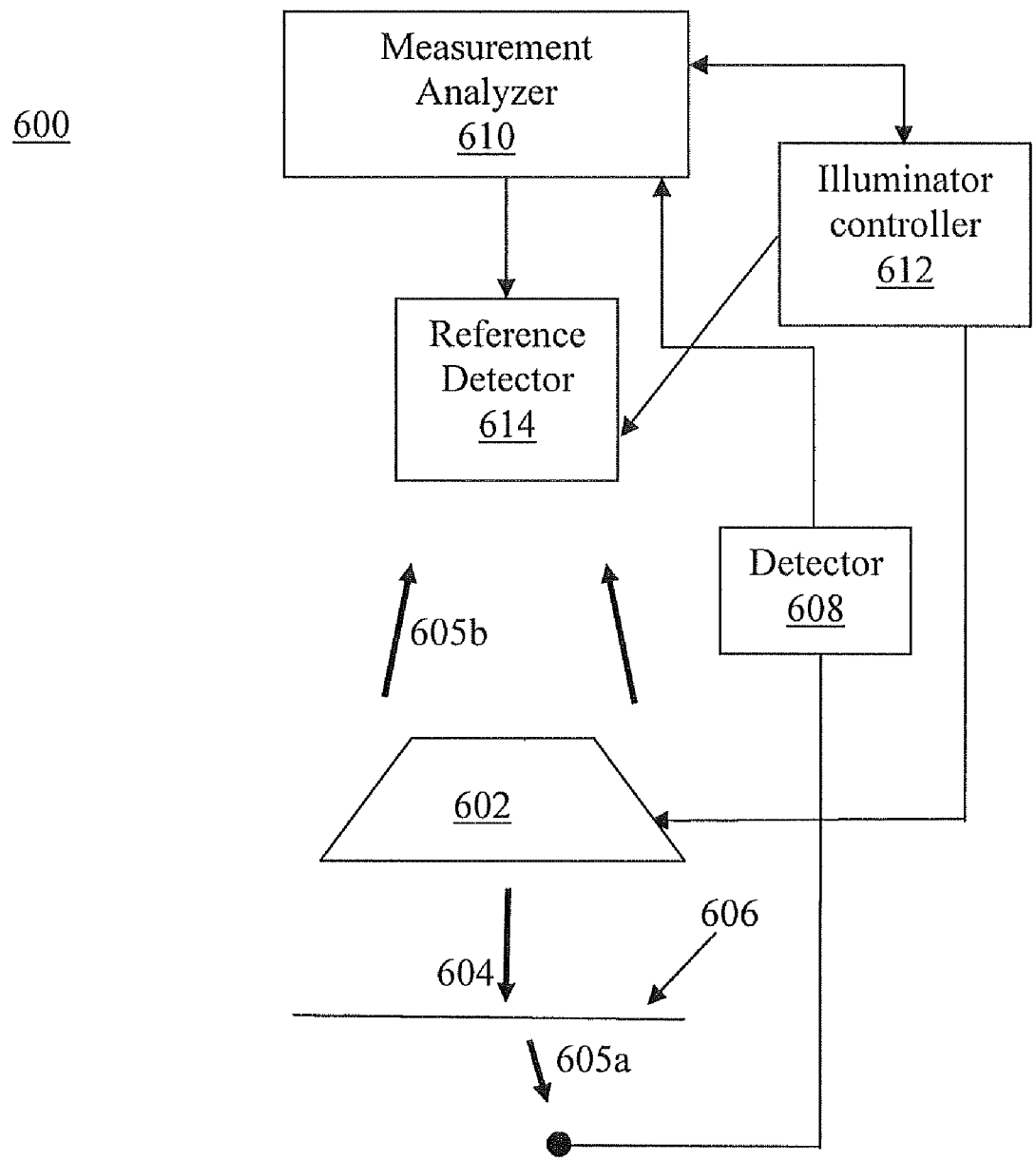
FIG. 6 is a generalized schematic of an illuminating device used to implement a fourth exemplary light source embodiment of the present invention.

Referring to FIG. 6, sensor 600 may include illuminating device 602 for providing a light beam 604 to illuminate a sample 606 at a pass-line. The illuminating device 602 provides a focused beam of light or collimated light beam, for example by utilizing one or more light emitting diodes. According to the fourth exemplary embodiment the detectors 608 may be located beyond the sample 606.

The beam of light 605a is detected by detector 608. The detector 608 supplies the measured values of light to a measurement analyzer 610. The measurement analyzer 610 uses the values of detected light to determine the characteristics of the sample 606. The measurement analyzer 610 may also regulate an illuminator controller 612. The measurement analyzer 610 may direct the illuminator controller 612 to cause the illuminating device 602 to emit light in different relative intensities at each of plural wavelength bands. The components of sample sensor 600 may incorporate aspects as previously described in sample sensors. A reference detector 614 may be used to provide a reference point for the measurement analyzer 610. The reference detector 614 may be positioned to receive an accurate sample 605b of the light emitted by illuminating device 602.

It will be understood that the foregoing is only illustrative of the principles of the invention and that various modifications can be made by those skilled in the art without departing from the scope and spirit of the invention. Accordingly, such embodiments will be recognized as within the scope of the present invention. Persons skilled in the art will also appreciate that the present invention can be practiced by other than the described embodiments, which are presented for purposes of illustration rather than of limitation and that the present invention is limited only by the claims that follow.

What is claimed is:

1. An apparatus for measuring one or more characteristics of a sample, the apparatus comprising:
    at least one light emitting diode configured to illuminate an area of the sample with first light, the first light including at least one band of ultraviolet light;
    a detector configured to receive second light and to measure a spectral power distribution of the second light in a plurality of wavelength bands substantially spanning at least a visible range of light to form a measured spectral power distribution, the second light based on the first light that has interacted with the sample; and
    an analyzer configured to determine the one or more characteristics of the sample using the measured spectral power distribution.

2. The apparatus of claim 1, wherein the at least one light emitting diode and the detector are on a same side of the sample.

3. The apparatus of claim 2, further comprising at least two backings on an opposite side of the sample, the backings having substantially different known reflectivities in the visible range;
    wherein the analyzer is configured to employ at least one measured spectral power distribution obtained with each of the backings.

4. The apparatus of claim 1, wherein the at least one light emitting diode and the detector are on different sides of the sample.

5. The apparatus of claim 1, further comprising at least one additional light emitting diode configured to emit at least one band of visible light.

6. The apparatus of claim 1, wherein the at least one light emitting diode is configured to emit the at least one band of ultraviolet light and at least one band of visible light.

7. The apparatus of claim 1, further comprising at least one additional light emitting diode configured to illuminate the area of the sample with light that substantially spans at least the visible range.

8. The apparatus of claim 1, further comprising a controller configured to control the at least one light emitting diode such that the at least one light emitting diode produces the at least one band of ultraviolet light in an intermittent manner.

9. The apparatus of claim 1, further comprising a controller configured to control operation of the at least one light emitting diode such that an intensity of the first light is varied.

10. The apparatus of claim 1, further comprising a controller configured to control operation of the at least one light emitting diode such that the first light has at least one desired spectral power distribution.

11. The apparatus of claim 10, wherein the analyzer is configured to employ multiple measured spectral power distributions obtained using multiple spectral power distributions of the first light.

12. The apparatus of claim 11, wherein the analyzer is configured to determine the one or more characteristics of the sample for a specified illumination that is not expressible as an exact linear combination of the spectral power distributions used to illuminate the sample, such that an interval of the one or more characteristics is determined for a range of linear combinations that bracket the specified illumination.

13. The apparatus of claim 1, wherein the first light also includes at least one band of visible light, and further comprising:
    one or more optical elements configured to divide the first light, such that a first portion of the first light is used to illuminate the sample and a second portion of the first light is not used to illuminate the sample; and
    a second detector configured to receive the second portion of the first light and to measure a spectral power distribution of the second portion of the first light in the plurality of wavelength bands substantially spanning at least the visible range to form a reference spectral power distribution.

14. The apparatus of claim 13, wherein the analyzer is configured to employ both the measured spectral power distribution and the reference spectral power distribution.

15. The apparatus of claim 13, further comprising a controller configured to control operation of the at least one light emitting diode such that the reference spectral power distribution is a desired spectral power distribution.

16. The apparatus of claim 1, wherein the at least one light emitting diode is provided with one or more optical elements configured to modify at least one characteristic of the first light.

17. The apparatus of claim 16, wherein the at least one modified characteristic of the first light comprises a spatial intensity distribution.

18. The apparatus of claim 16, wherein the at least one modified characteristic of the first light comprises a spectral power distribution of the first light.

19. The apparatus of claim 16, wherein the at least one modified characteristic of the first light comprises a state of polarization.

20. A method for detecting one or more characteristics of a sample, comprising:
    supplying power to at least one visible light emitting diode;
    directing a first beam of light from the at least one visible light emitting diode onto a sample;
    supplying power to at least one ultraviolet light emitting diode;
    directing a second beam of light from the at least one ultraviolet light emitting diode onto the sample;
    detecting visible light and ultraviolet light that have interacted with the sample, wherein the visible light and ultraviolet light that have interacted with the sample are based on the first and second beams of light; and
    determining the one or more characteristics of the sample based on the detected visible light and ultraviolet light.

21. The method of claim 20, wherein supplying power to the at least one ultraviolet light emitting diode is performed intermittently.

22. The method of claim 20, wherein:
supplying the power to the at least one visible light emitting diode comprises supplying the power via a first circuit board; and
supplying the power to the at least one ultraviolet light emitting diode comprises supplying the power via a second circuit board.

23. The method of claim 20, wherein supplying the power to the at least one ultraviolet light emitting diode is performed by varying a current supplied to the at least one ultraviolet light emitting diode.

* * * * *